United States Patent [19]

Umezawa et al.

[11] Patent Number: 4,559,362

[45] Date of Patent: Dec. 17, 1985

[54] IMMUNOPOTENTIATOR

[75] Inventors: Hamao Umezawa; Tomio Takeuchi; Masaaki Ishizuka, all of Tokyo, Japan

[73] Assignee: Zaidan Hojin Biseibutsu Kagaku Kenkyu Kai, Tokyo, Japan

[21] Appl. No.: 550,184

[22] Filed: Nov. 9, 1983

[30] Foreign Application Priority Data

Nov. 27, 1982 [JP] Japan .................................. 57-208254

[51] Int. Cl.$^4$ .............................................. A61K 31/13
[52] U.S. Cl. ..................................... 514/674; 514/885
[58] Field of Search .................. 424/325, 674; 514/885

[56] References Cited

U.S. PATENT DOCUMENTS 4,013,507 3/1977 Rembaum ........................... 435/194

OTHER PUBLICATIONS

Duffy et al., Chem. Abst., 76:94478f, 1972.
Swanson et al., Chem. Abst., 93:231724a, 1980.
Merck Index, tenth ed., 1983, No. 8586.
Oriol-Audit, Biochem. and Biophy., Res. Com. 105(3), 1096-1101, 1982.

Primary Examiner—Albert T. Meyers
Assistant Examiner—John W. Rollins
Attorney, Agent, or Firm—Henry C. Nields

[57] ABSTRACT

This invention relates to an immunopotentiator or an immunopotentiating method using spermidine or its pharmacologically acceptable salt as an active ingredient.

3 Claims, No Drawings

IMMUNOPOTENTIATOR

DETAILED DESCRIPTION OF THE INVENTION

This invention relates to an immunopotentiator containing spermidine or its pharmacologically acceptable salt as active ingredient.

The present inventors have made an extensive research for obtaining substances having immunopotentiating action, and found that spermidine represented by the following formula;

$$H_2N-(CH_2)_3-NH-(CH_2)_4-NH_2$$

possesses the effect of enhancing immunity in living body. This discovery has led the inventors to complete this invention.

The immunopotentiator of this invention inhibits suppressor cells, activates the alternative pathway of the complement system, and augments the production of interleukine-2. These features potentiates immunity, permitting the effective treatment of various immunity-associated diseases, such as cancer, immunodeficiency, and various infective diseases Spermidine for use in this invention can be used in the form of its pharmacologically acceptable salts. The salts include, for example, salts with inorganic acids such as hydrochloric acid, sulfuric acid, phosphoric acid and boric acid, and salts with organic acids such as acetic acid, citric acid, tartaric acid, and glutaric acid.

The immunopotentiators of the present invention may contain the above-mentioned active ingredients in combination with medical adjuvants, such as carriers, stabilizers or excipients, which turn them into liquids such as syrups and injections, solids such as tablets, granules, powders, capsules and suppositories, or ointments.

The immunopotentiator comprise 0.01-10% prefereably 0.05-5% by weight of spermidine or its pharmacologically acceptable salt and 99.99-90% preferably 99.95-95% by weight of pharmacologically acceptable adjuvents. These preparations may be injected or administered by the oral or percutaneous route.

Spermidine used in this invention has a very low toxicity. It is not toxic at a dose of 250 mg/kg when given intravenously to mice.

The immunopotenciating method of the present invention comprises administering spermidine or its pharmaceutically acceptable salt in an effective amount to a warm-blooded animal including a human.

The dose of spermidine varies depending on the age, symptoms and said animals. The dose is usually 0.01 mg/kg/day—50 mg/kg/day of the body weight of said animal. The single dose for an adult of a human is 0.03 to 800 mg which may be given once or several times daily depending on the symptoms.

The immunopotentiator of this invention may be used either singly or in combination with other anticancer drugs such as bleomycin.

The pharmacological effects of spermidine will be illustrated by reference to the following experimental examples, in which spermidine was administered as its phosphate dissolved in physiological saline.

A. Immunopotantiating action

1. Action on cell-mediated immunity (a) Effect on delayed hypersensitivity of sheep erythrocytes.

In accordance with the method of Lagrange et al. (Lagrange, P. H., Mackaness, G. B., and Miller, T. E.: Influence of dose and route of antigen injection on the immunological induction of T cells. J. Exp. Med. 139, 528-542, 1974), the effect of spermidine on cellular immunity was investigated using as its index the degree of delayed-type hypersensitivity (DTH) to sheep erythrocytes as the antigen. $CDF_1$ mice (8 weeks old, female) were intravenously injected with $10^5$ or $10^8$ sheep erythrocytes for immunization, and at the same time, were intraperitoneally injected with spermidine. Four days later, the soles of the mice were subcutaneously injected with $10^8$ sheep erythrocytes to induce the DTH reaction. Twenty four hours later, swellings on the soles were measured with a caliper to evaluate the effect of spermidine. The results are shown in Table 1.

TABLE 1

| | Efficacy of spermidine in establishing DTH to sheep erythrocytes | | |
|---|---|---|---|
| Imunogen | Spermidine (μg/mouse) | Swelling on the sole (× 0.1 mm) | % increase |
| $10^5$ sheep erythrocytes | 0 | 6.4 ± 0.6 | 100 |
| $10^5$ sheep erythrocytes | 0.01 (0.0005) | 5.8 ± 0.4 | 91 |
| $10^5$ sheep erythrocytes | 0.1 (0.005) | 9.4 ± 0.7 | 147 |
| $10^5$ sheep erythrocytes | 1 (0.05) | 8.5 ± 0.7 | 133 |
| $10^5$ sheep erythrocytes | 10 (0.5) | 8.9 ± 0.7 | 139 |
| $10^5$ sheep erythrocytes | 100 (5) | 8.1 ± 1.1 | 126 |
| $10^5$ sheep erythrocytes | 1000 (50) | 7.1 ± 0.3 | 111 |
| $10^8$ sheep erythrocytes | 0 | 3.1 ± 0.4 | 48 |
| $10^8$ sheep erythrocytes | 0.01 (0.0005) | 4.5 ± 0.2 | 70 |
| $10^8$ sheep erythrocytes | 0.1 (0.005) | 5.3 ± 0.3 | 83 |
| $10^8$ sheep erythrocytes | 1 (0.05) | 6.3 ± 0.3 | 98 |
| $10^8$ sheep erythrocytes | 10 (0.5) | 6.4 ± 0.06 | 100 |
| $10^8$ sheep erythrocytes | 100 (5.0) | 6.4 ± 0.4 | 100 |
| $10^8$ sheep erythrocytes | 1000 (50) | 7.4 ± 0.5 | 116 |

The above table shows that for the group of mice immunized with $10^5$ sheep erythrocytes, the amount enough to produce the optimal reaction, spermidine exhibited a significant effect of enhancing cellular immunity in doses of 0.1 to 100 μg/mouse, but showed no enhancing effect in a dose of 0.01 or 1000 μg/mouse.

For the group immunized with $10^8$ sheep erythrocytes, the amount enough to augment the production of suppressor cells against DTH and suppress this reaction, spermidine in doses of 0.1 to 1000 μg/mouse exhibited a marked effect of strengthening cellular immunity, compared with the control group also receiving $10^8$ sheep erythrocytes. Particularly, the doses of 10 to 1000 μg/mouse produced a reaction comparable to that for the group immunized with $10^5$ erythrocytes, the amount enough to produce the optimal reaction.

These results demonstrate that spermidine in doses of 5 to 0.005 mg/kg enhances normal cellular immunity, and that the doses of 50 to 0.5 mg/kg inhibit the suppression of cellular immunity by suppressor cells, thus augmenting a depressed DTH reaction and recovering it to normal condition.

(b) Effect of inhibiting the elevation of suppressor cells against DTH

Experiments were conducted to transfer suppressor cells, in accordance with the method of Yamaguchi et al. (Yamaguchi, K. and Kishimoto, S.: Distinction between suppressors of the delayed-type hypersensitivity and the humoral response to sheep erythrocytes. Immunology. 35, 721-731, 1978). $CDF_1$ mice (8 weeks old, female) were intravenously administered with $10^8$ sheep erythrocytes, the amount enough to induce the elevation of suppressor cells against DTH. The objective was to promote the production of suppressor cells. Two days later, supermidine was intraperitoneally injected once daily, and this treatment was continued for 3 days. Five days later, spleen cells were collected from the mice, and $4.5 \times 10^7$ cells of them were transferred to normal syngenic mice by i.v. injection. Simultaneously, $10^5$ sheep erythrocytes, the amount enough to obtain the optimal reaction, was i.v. injected for immunization.

Four days later, $10^8$ sheep erythrocytes were subcutaneously injected to the soles of the mice to induce the reaction. Twenty-four hours later, swellings on the soles were measured to evaluate the efficacy of spermidine. The results are shown in Table 2.

TABLE 2

Inhibitory effect of spermidine on the elevation of suppressor cells against DTH

| Transferred cells | Treatment | Swelling on the sole (× 0.1 mm) | % suppression |
|---|---|---|---|
| Normal spleen cells | — | 13.8 ± 1.1 | 0 |
| Suppressor cells | — | 6.5 ± 0.4 | 53 |
| Suppressor cells | Spermidine 10 μg | 8.0 ± 0.3 | 42 |
| " | Spermidine 100 μg | 10.2 ± 0.3 | 26 |
| " | Spermidine 1000 μg | 10.9 ± 0.8 | 21 |

The above table shows that in the mice to which suppressor cells have been transferred, DTH reaction declined to about ½ of the normal level, indicating a clear suppressive action of the suppressor cells. The suppressive action was weak in the mice which received spleen cells that had been obtained from the mice given spermidine. This fact demonstrated spermidine to have in inhibitory effect on the elevation of suppressor cells. The inhibitory effect was marked particularly in doses of 100 to 1000 μg/mouse (about 5 to 50 mg/kg) in which suppression ranged from about ¼ to 1/5.

The above findings demonstrate spermidine to have an inhibitory effect on the elevation of suppressor cells against cellular immunity and to be useful in the treatment of immunodeficiency associated with suppressor cells.

2. Action on the activation of the alternative pathway of the complement system

The effect of spermidine on the activation of the alternative pathway of the complement system was investigated in accordance with the method of Platts-Mills and Ishizaka (Platt-Mills, T. A. E. and Ishizaka, K.: Activation of the alternative pathway of human complement by rabbit cells. J. Immune. 113, 348-358, 1974).

Spermidine was added to normal human serum in EGTA buffer solution, and the mixture was heated at 37° C. for 60 minutes. Rabbit blood cells were then added to the mixture. The degree of hemolysis was measured with a spectrophotometer at 412 nm to evaluate the effect of spermidine. The results are shown in Table 3.

TABLE 3

Activation of the alternative pathway of the complement system by spermidine

| Spermidine (mg/ml) | % consumption of complement component | Degree of activation C3 |
|---|---|---|
| 8 | 83.6 | +++ |
| 4 | 66.1 | ++ |
| 2 | 0 | — |

Table 3 shows that spermidine added in amounts of 4 to 8 mg/ml clearly activates the alternative pathway of complement, suggesting that spermidine acts on complement and enhances immunity.

3. Action on the production of lymphokine (interleukine-2)

The effect of spermidine on the production of interleukine was investigated in accordance with the method of Larsson et al. (Larsson, E-L: Mechanism of T cell activation II. Antigen- and lectin-dependent acquisition of responsiveness to TCGF is a nonmitogenic, active response of resting T cells. J. Immunol. 126, 1323-1326, 1981).

Spermidine in a varying concentration was added to $1 \times 10^7$ spleen cells/ml of $CDF_1$ mice. In the presence or absence of added concanavalin A (2 μg/ml), the stimulant of interleukine-2 production, the cells were then cultured in a cell incubator kept at 37° C. and at a carbon dioxide concentration of 5% for 24 hours. After completion of the incubation, α-methylmannoside was added to the supernatant to inactivate concanavalin A. The supernatant was collected to examine its interleukine-2 activity. The interleukine-2 activity was determined by the activity of promoting the proliferation of T blast cells and the activity of promoting the division of thymocytes. The latter two activities were determined by measuring $^3$H-thymidine incorporations to both types of cells. The results are shown in Table 4.

TABLE 4

| Effect of spermidine on interleukine-2 production | | | |
|---|---|---|---|
| Spermidine (μg/ml) | Con A (2 μg/ml) | $^3$H—thymidine incorporation (%) | |
| | | T blast cells | Thymocytes |
| — | — | 100 | 100 |
| 0.001 | — | 137 | 171 |
| 0.01 | — | 152 | 255 |
| 0.1 | — | 166 | 281 |
| 1 | — | 136 | 90 |
| — | + | 100 | 100 |
| 0.001 | + | 94 | 126 |
| 0.01 | + | 153 | 130 |
| 0.1 | + | 157 | 149 |
| 1 | + | 152 | 135 |

As seen from the above table, the addition of spermidine to spleen cell cultures increased interleukine-2 production in either experimental system, irrespective of stimulation by Con A. The optimal concentration of spermidine was 0.1 μg/ml. These findings suggested that spermidine increases interleukine-2 production and enhance immune response mediated by interleukine-2.

B. Carcinostatic action

1. Action on cultured cancer cells

A study was conducted on the growth inhibitory effect of spermidine on cultures of IMC cancer cells and L-1210 cells. IMC cancer cells were cultured in an RPMI 1640 medium containing 10% bovine fetus serum and 2-mercaptoethanol, and L-1210 cells in an MEM medium containing 10% calf serum, for 48 hours at 37° C. in 5% carbon dioxide. The number of cultured cells was counted with a Coulter counter to evaluate the degree of cell proliferation. Spermidine was added at the start of incubation.

The concentration of spermidine at which 50% of the original cells were inhibited from growth was 2.4 µg/ml for IMC cancer cells, and 2.8 µg/ml for L-1210 cells.

2. Action on transplanted mouse tumor in mice (a) The antitumor effect of spermidine was investigated on IMC carcinoma successively transplanted into $CDF_1$ mice and on S180 sarcoma transplanted into ICR mice. $1 \times 10^6$ tumor cells of each of the above type were transplanted subcutaneously into such mice (Day 0). From Day 1 onwards, spermidine was intraperitoneally injected a total of 10 times (once daily on alternative days). Thirty days after transplantation of tumor cells, the tumor was removed and weighed to evaluate the effect of spermidine. The results are shown in Table 5.

TABLE 5

| Spermidine (mg/kg/day) | Antitumor action of spermidine Weight of tumor ± S.D. (% inhibition) | |
|---|---|---|
| | IMC carcinoma | S-180 sarcoma |
| 0 | 6935 ± 3316 | 5699 ± 1292 |
| 0.05 | 5112 ± 2263 (26) | 5193 ± 1522 (9) |
| 0.5 | 2893 ± 964 (58) | 3689 ± 1331 (35) |
| 5 | 4125 ± 1852 (40) | 2087 ± 1040 (63) |
| 50 | 3886 ± 1351 (44) | 3245 ± 1106 (43) |

From the above table, spermidine was found to give tumor growth inhibitions of 30 to 60% in doses of 0.05 to 50 mg/kg/day.

(b) $1 \times 10^2$ mouse leukemia L-1210 cells were transplanted into $CDF_1$ mice by subcutaneous injection (Day 0). From Day 1 onwards, 0.5 to 5 mg/kg of spermidine was administered in total of 10 times, once daily on alternative days, to investigate on the number of days the mice survived. The dose of 5 mg/kg was found to produce complete remission of 3 out of 10 mice. The results are shown in Table 6.

TABLE 6

| Effect of spermidine on mouse leukemia L-1210 | | | |
|---|---|---|---|
| Spermidine (mg/kg) | Survival period (days) | Increase of life span (%) | Survival rate on Day 60* |
| 0 | 14.7 ± 1.4 | 100 | 0/10 |
| 0.5 | 16.0 ± 3.1 | 109 | 1/10 |
| 5 | 15.2 ± 2.2 | 104 | 3/10 |

*Mice that survived for 60 days are excluded from the calculation of increases of life span.

(c) $1 \times 10^6$ IMC cancer cells were transplanted into $CDF_1$ mice by intraperitoneal injection (Day 0). Bleomycin (5 mg/kg) was administered once daily for 5 consecutive days, and spermidine (5 mg/kg) was administered a total of 10 times on alternative days. The effect of concomitant treatment with spermidine and the anticancer drug was evaluated by considering the number of days that the mice survived. The results are given in Table 7.

TABLE 7

| Effect of concomitant treatment with bleomycin and spermidine on IMC ascites tumor | | | | |
|---|---|---|---|---|
| Spermidine (5 mg/kg) | Bleomycin (5 mg/kg) | Survival period (days) | Increase of life span (%) | Survival rate on Day 60* |
| − | − | 17.7 ± 1.8 | 100 | 0/10 |
| − | + | 31.2 ± 9.4 | 176 | 0/10 |
| + | − | 20.1 ± 2.3 | 114 | 0/10 |
| + | + | 39.9 ± 13.5 | 225 | 4/10 |

The group administered with bleomycin alone had a life span increase of 76% compared with the control group. The group administered with spermidine alone showed a life span increase of 14% against the control group. For the group administered with both spermidine and bleomycin concomitantly, 4 out of 10 mice survived for 60 days, demonstrating the concomitant use of these drugs to be clearly effective. The above findings made it clear for spermidine to inhibit suppressor cells, activate the alternative pathway of complement, and augment the production of interleukine-2, thereby enhancing cell-mediated immunity and showing an antitumor effect against various types of tumor.

These experimental examples clearly indicate the usefulness of spermidine in immunotherapy and chemotherapy of tumor. Spermidine can be also used in the treatment of various types of immunodeficiency, viral infection, and bacterial infection.

Preparations comprising spermidine and its salts will be described below.

To prepare injections, pH adjustors, buffers, and if desired, stabilizers, isotonizers, local anesthetics, and other adjuvants may be added to the aforementioned active ingredients to form them into aqueous solutions, which are then filled into empty ampoules to make injections. The above aqueous solutions may be freezed-dried to make lyophilized injections.

For the preparation of orally administrable solids, excipients such as lactose or corn starch, and if desired, binders, disintegrators, lubricants, colorants and correctives may be added to the active ingredients, followed by forming the mixtures into tablets, granules, powders, and capsules by customary methods.

In the preparation of rectal suppositories, excipients, and if desired, surfactants may be added to the active ingredients, and the mixtures are made into suppositories by customary methods.

EXAMPLE 1

One gram of spermidine phosphate and 50 g of mannitol were dissolved in 1000 ml of sterilized water to obtain an injection for intramuscular administration.

EXAMPLE 2

One gram of spermidine phosphate, 5 g of bleomycin and 10 g of mannitol were dissolved in distilled water to make a 1000 ml solution. The solution was sterilized, and put in empty vials in aliquots of 1 ml. Then, the contents were freezedried, and the vials were sealed. The resulting preparations was used as injections after having dissolved in distilled water.

EXAMPLE 3

One part of spermidine phosphate, 200 parts of lactose, 50 parts of corn starch and 3 parts of polyvinyl pyrrolidone were mixed, and the mixture was pelleted according to customary method together with ethanol follwed by drying and sixing. One % of magnesium stearate was added to the pellets, and the mixture was formed into tablets with an active ingredient content of 3.6 mg each by a customary method.

EXAMPLE 4

One part of spermidine phosphate and 900 parts of lactose were mixed thoroughly. The mixture was sifted through a 50-mesh sieve to obtain a powdery preparation.

EXAMPLE 5

0.5 g of spermidine phosphate, 300 g of sugar, 1 g of citric acid, and orange extract were dissolved in distilled water to make a 1000-ml solution which serves as a syrup.

EXAMPLE 6

One part of spermidine phosphate and 300 parts of cacao butter were mixed to form a melt. This material was formed by a customary method into suppositories weighing 2 g each.

We claim:

1. An immunopotenciating method which comprises administering spermidine or its pharmacologically acceptable salt in an effective amount to a warm-blood animal having an immunity-associated disease.

2. The method of claim 1 wherein said compound is administered in amount between 0.005 mg/kg/day—50 mg/kg/day of body weight said animal.

3. The method of claim 2 wherein said compound is administered in amount between 0.01 mg/kg/day—50 mg/kg/day of the body weight of said animal.

* * * * *